United States Patent
Weiss et al.

(10) Patent No.: US 8,401,647 B2
(45) Date of Patent: Mar. 19, 2013

(54) ACTIVE MEDICAL IMPLANT

(75) Inventors: Ingo Weiss, Berlin (DE); Stefan Knorr, Berlin (DE)

(73) Assignee: Biotronik CRM Patent AG, Baar (CH)

( * ) Notice: Subject to any disclaimer, the term of this patent is extended or adjusted under 35 U.S.C. 154(b) by 381 days.

(21) Appl. No.: 12/707,127

(22) Filed: Feb. 17, 2010

(65) Prior Publication Data
US 2010/0217354 A1     Aug. 26, 2010

(30) Foreign Application Priority Data
Feb. 20, 2009    (DE) .......................... 10 2009 001 042

(51) Int. Cl.
*A61N 1/08*      (2006.01)
(52) U.S. Cl. .......................................... 607/35
(58) Field of Classification Search .................. 607/33, 607/35
See application file for complete search history.

(56) References Cited

U.S. PATENT DOCUMENTS

| | | | |
|---|---|---|---|
| 3,421,512 A * | 1/1969 | Frasier | 607/35 |
| 3,486,506 A * | 12/1969 | Auphan | 607/19 |
| 3,554,199 A * | 1/1971 | Auphan | 607/19 |
| 3,659,615 A * | 5/1972 | Enger | 607/35 |
| 3,693,625 A * | 9/1972 | Auphan | 607/19 |
| 3,943,936 A * | 3/1976 | Rasor et al. | 607/35 |
| 4,690,143 A * | 9/1987 | Schroeppel | 607/5 |
| 5,628,777 A | 5/1997 | Moberg et al. | |
| 5,749,909 A * | 5/1998 | Schroeppel et al. | 607/33 |
| 6,546,286 B2 * | 4/2003 | Olson | 607/5 |
| 6,556,867 B1 * | 4/2003 | Kohls | 607/35 |
| 2005/0256549 A1 * | 11/2005 | Holzer | 607/35 |
| 2006/0136005 A1 | 6/2006 | Brisken et al. | |
| 2006/0217776 A1 | 9/2006 | White et al. | |
| 2007/0276444 A1 | 11/2007 | Gelbart et al. | |
| 2007/0293904 A1 | 12/2007 | Gelbart et al. | |

FOREIGN PATENT DOCUMENTS

| | | |
|---|---|---|
| DE | 10 2006 062 541 | 8/2007 |
| WO | 2007/109272 | 9/2007 |

OTHER PUBLICATIONS

European Search Report and Notes to the European Search Report on European Patent Application No. EP 10 15 2262, dated Jan. 16, 2013 (6 pages).

* cited by examiner

*Primary Examiner* — Brian T Gedeon
(74) *Attorney, Agent, or Firm* — Buchanan Ingersoll & Rooney PC

(57) ABSTRACT

An active medical implant, in particular a medical electronic device having a power supply which has a mechanical vibrator or rotor which is induced to vibrate and/or rotate by movements of the patient wearing the implant and/or external excitation and is energetically connected to an electronic consumer and/or an energy storage mechanism, such that a portion of the kinetic energy generated by the vibration and/or rotation is input into the consumer and/or energy storage mechanism.

19 Claims, 10 Drawing Sheets

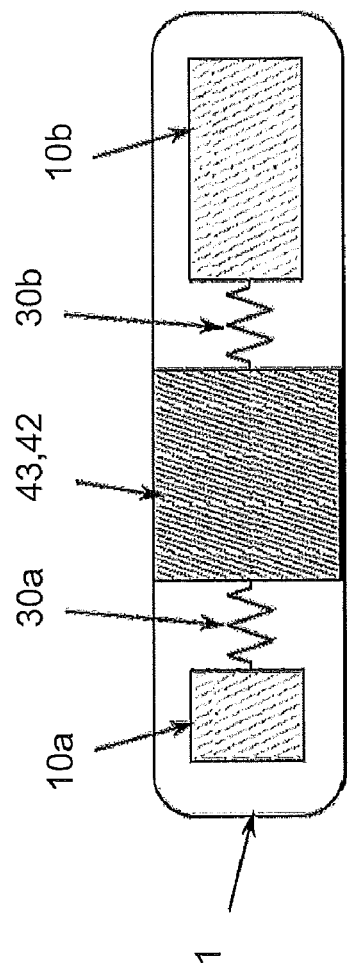
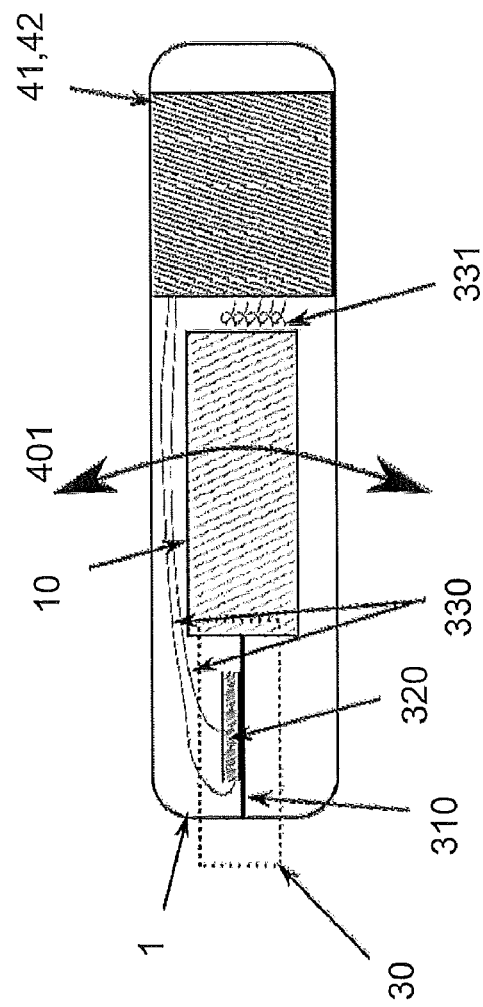
Fig. 2
Fig. 3

ACTIVE MEDICAL IMPLANT

CROSS-REFERENCE TO RELATED APPLICATIONS

This application claims the priority of German Patent Application No. DE 10 2009 001 042.4, filed on Feb. 20, 2009 in the German Patent Office, the disclosure of which is incorporated herein in its entirety by reference.

FIELD OF THE INVENTION

The invention relates to an active medical implant, in particular a medical electronic device such as a cardiac pacemaker, an implantable defibrillator, an implantable medication dosing pump or a similar device.

BACKGROUND OF THE INVENTION

For their power supply, active medical implants either have an energy storage mechanism (battery, capacitor) or are constantly supplied with power transcutaneously (via cable, HF, alternating magnetic field). A transcutaneous power supply can be used for only short periods of time because there is a high risk of infection or the constant HF burden can lead to tissue damage. Therefore, this has not been successful in medical practice on a large scale.

Energy storage mechanisms become depleted after a certain amount of time and must be replaced or recharged. Replacing the energy storage mechanism is necessarily associated with explantation of the entire device and reimplantation of the same device and/or a replacement device. In the past, this was the most common procedure, but it is complicated, expensive and associated with medical risks and considerable discomfort for the user of the implant.

An extracorporeal primary coil and a secondary coil inside the implant are generally used to charge a rechargeable energy storage mechanism (battery) of an active implant. Power is transmitted from the primary coil to the secondary coil through an alternating magnetic field. The maximum transmissible energy is limited by heating of the tissue in the passage of energy. A charging cycle of the energy storage mechanism may also become very long due to the low energy transfer rate. Conventional rechargeable chemical cells have a longer lifetime if they are charged regularly and frequently and thus always have a high level of charge. Depending on the use of the transcutaneous energy transfer, the rechargeable cell may become very highly discharged before the charging operation, thus reducing the lifetime of the cell. Maintaining regular charging cycles to maintain the function of the implant is the responsibility of the physician or the patient. In the physician's practice, it requires a great deal of organizational effort and discipline on the part of the patient but this is often not adequately ensured in practice.

The present invention is directed toward overcoming one or more of the above-identified problems.

SUMMARY OF THE INVENTION

Therefore, an object of the invention is to provide a medical implant which has been improved with regard to its power supply and whose operational capability is permanently secured with little medical, technical and organizational complexity in particular.

This object is achieved by an active medical implant having the features of claim 1. Expedient further embodiments of the inventive idea are the subject of the dependent claims.

According to the invention, a mechanical system capable of vibration or rotation is used in the implant. Mechanical vibrations are converted to electricity by a mechanical-electric converter, and this electricity is then available to the implant. Piezoelectric materials or electromagnetic converters, for example, may be used as the mechanical-electric converters.

This electricity may be used to charge an energy storage mechanism, e.g., a battery or an energy storage capacitor, or to partially cover the continuous power consumption by the implant. As an alternative, it may also be possible for the energy storage mechanism to have a means of storing mechanical energy, in particular a flywheel or the like, to which a mechanical-electric converter is allocated for converting stored mechanical energy into electric operating energy for the consumer.

It is possible to provide for the vibrator or rotor to be arranged in a shared housing together with the active electric components of the implant. However, the vibration-capable system may also be implanted as a separate IMD outside of the active implant, and the power may be transmitted to the electronic system of the active implant. In this way, the vibration-capable system can be attached closer to a bone, for example, and can be better linked to high-energy movements of the body.

In another embodiment, multiple vibrators and/or rotors having different directions of vibration and/or axes of movement and/or different natural frequencies may be provided. Alternatively or in combination with that, it is possible to provide for the/a vibrator to be designed to be capable of vibration in more than one direction, in particular in three dimensions.

Finally, an embodiment in which the vibrator has an independently variable direction of vibration and/or the/a rotor has an independently variable axis of rotation is also possible for optimum utilization of various movements of the patient in different body positions to generate power for the implant. It is provided here in particular that the vibrator having a variable direction of vibration and/or the rotor having a variable axis of rotation will have means for adjusting the direction of vibration and/or the axis of rotation as a function of the position of the patient's body and/or movements of the patient wearing the implant.

With regard to the structural implementation of the mechanical energy source, in another embodiment of the invention, it is provided that the/a vibrator or rotor comprises function components and/or supporting components of the implant that are suspended in a rotatable manner in a housing, so they are rotatable and/or capable of vibration. This may be done in particular in such a way that the/a vibrator or rotor comprises a carrying frame of the implant with function components mounted therein.

The mass of the vibrator may thus be increased and the natural frequency may be reduced. This may go so far that the vibration-capable system is formed by the entire internal structure of the implant (energy storage mechanism, electric circuit, mounting frame, etc.).

According to another embodiment, which is aimed at the most efficient possible utilization of the energy of various movements of the patient to treat the implant, the/each vibrator or rotor is designed to receive external excitation with a frequency tuned to its natural frequency. Specifically an electromechanical converter, in particular a piezo element or an electromagnetic converter is assigned to the externally excitable vibrator or rotor for excitation by an external alternating electromagnetic field.

The invention makes possible, among other things:
- construction of active implants having a primary battery with a longer lifetime than before,
- construction of active implants with a rechargeable cell, where the energy for charging the battery is obtained from movements by the patient,
- construction of implants having a longer life expectancy than in the past, without the implant having to rely on regular charging operations from the outside. This also eliminates the thermal burden on the tissue in charging (e.g., due to eddy currents in the metallic housing, which are induced by an alternating magnetic field).

With regard to the dimensioning of the mechanical system, it is advantageous if the mass of the vibration-capable system constitutes more than 5% of the total mass of the implant. In addition, it may be advantageous if the system has a natural frequency of less than 10 Hz.

BRIEF DESCRIPTION OF THE DRAWINGS

Advantages and expediencies of the invention are also derived from the following description of preferred exemplary embodiments on the basis of the figures, in which:

FIG. 2 shows a schematic diagram of a second embodiment of the inventive implant;

FIG. 3 shows a detailed diagram of a first version of the first embodiment;

FIG. 8 shows a schematic diagram of a version of the first embodiment that has been modified in comparison with the design mentioned last;

DETAILED DESCRIPTION OF THE INVENTION

Figure 1A:
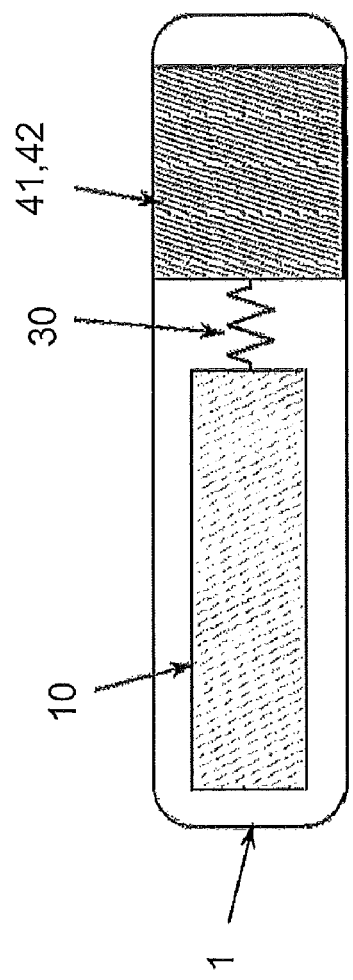
FIGS. 1A and 1B show a schematic diagram of a first embodiment of the inventive implant.

FIG. 1A shows an active implant 1 having a housing 1a, which holds a movable component mass 10. The mass 10 is connected to additional components 41, 42 fixedly installed in the housing or connected to the housing 1a itself via a coupling system 30. The coupling system converts the energy of mechanical vibration into electricity and makes this power available to the implant electronic system 41. The energy may be stored in a power reservoir 42. This reservoir may be an electrochemical cell or a capacitor.

Figure 1B:
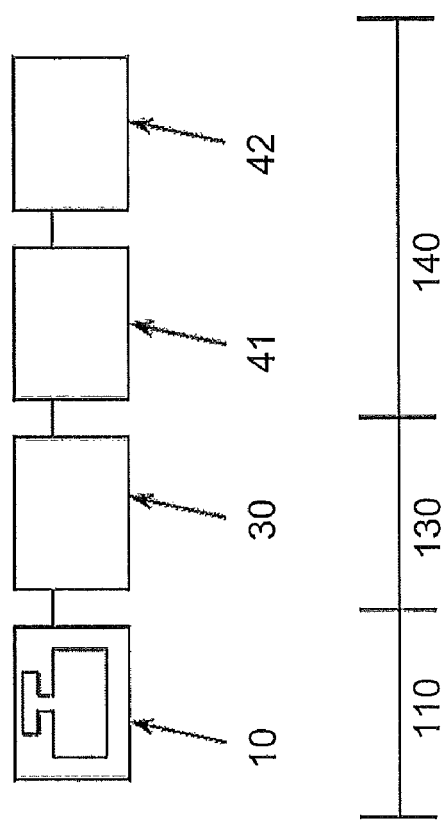

The system illustrated in FIG. 1B may be described physically by a vibration-capable mass 10 coupled to a mechanical-electric converter 30, an electric circuit 41 and a power reservoir 42. In the first section of the system, the mass may execute movements. The energy of the movements is converted into electricity by the mechanical-electric converter in the second portion 130. In the last portion 140, electricity is utilized by the implant electronic system 41 and/or stored in the power reservoir 42.

In addition to the mechanical-electric converter, the coupling system also contains a restoring system (not shown here) which brings the movable mass into a certain resting position. Such a restoring system may include a spring of any design. Plate springs are especially suitable because they have a low overall height.

For resetting, other principles may also be utilized, e.g., two mutually repelling magnets. Such a system is nonlinear, in contrast with a spring, and thus may induce a broadband vibration. The springs may preferably be made of a nonmagnetic material, e.g., brass alloys, titanium alloys, plastic or ceramic. The vibration may essentially occur about any axis in the implant or along any axis in the implant.

An implant having a plurality of vibration-capable component systems, as illustrated schematically in FIG. 2, operates essentially like the system presented above, but there are two masses 10a, 10b and two respective coupling systems 30a, 30b. The implant electronic system 43 is designed to utilize electricity from more than just one coupling system.

To be somewhat more precise, the embodiment of an implant having a vibration-capable component system is shown in FIG. 3 and described below. The vibration-capable mass 10 is connected to the implant housing via a coupling system 30. The coupling system consists of a plate spring 310 and a piezoelectric element 320. This converter element converts mechanical energy into electricity. The two terminals of the element 320 are connected by electric leads 330 to the implant electronic system 41. The electric connections 331 are preferably attached where the mechanical stress due to the vibrating component system is the lowest. If the mass 10 consists partially of electronic components of the implant electronic system 41 or the power reservoir 42, then several movable electric connections 331 between the vibration-capable mass 10 and the fixedly installed parts of the electronic system are used. The figures are to be understood only as basic diagrams in this sense.

The mass 110 may move as shown 401. Due to the movement of the mass 10, the spring 310 and thus the piezoelectric converter 320 mounted on it undergo deformation. In the interior of the converter, a strong electric field is created and a voltage is built up between the two contacts. If the mass 10 vibrates back and forth, an alternating voltage is applied to the contacts of the converter 320.

Instead of a piezoelectric element 320, a stack of several piezoelectric elements may also be used. Instead of individual ceramic disks, piezoelectric fibers may also be used, e.g., as a so-called "macro fiber composite." Depending on the embodiment of the piezoelectric converter 320, it may also assume the function of the spring 310 and may even replace it.

Figure 4:
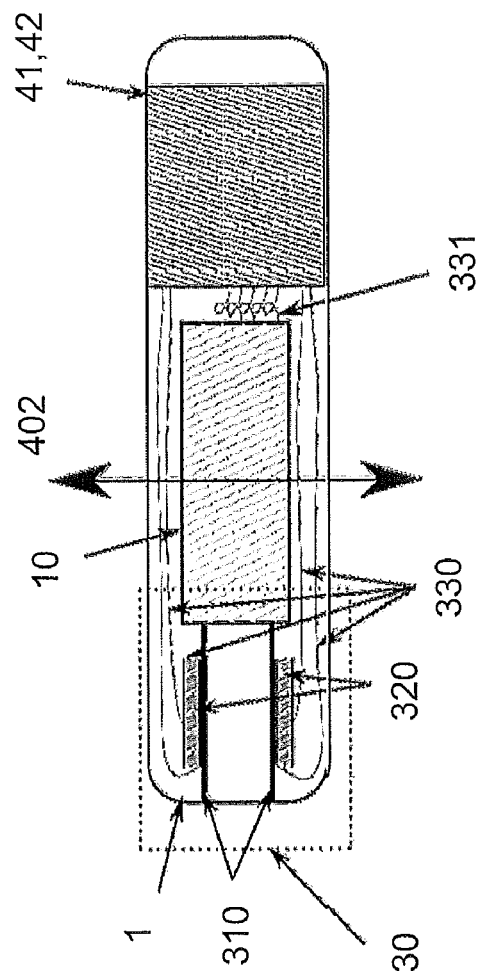
FIG. 4 shows a detailed diagram of a second version of the first embodiment.

Instead of one spring, as shown in FIG. 4, multiple springs 310 may also be used. Thus, in this example, the movement of the mass 10 is converted from rotation 401 into translation 402. The piezoelectric converter 320 need not be mounted on all springs 310.

Figure 5:
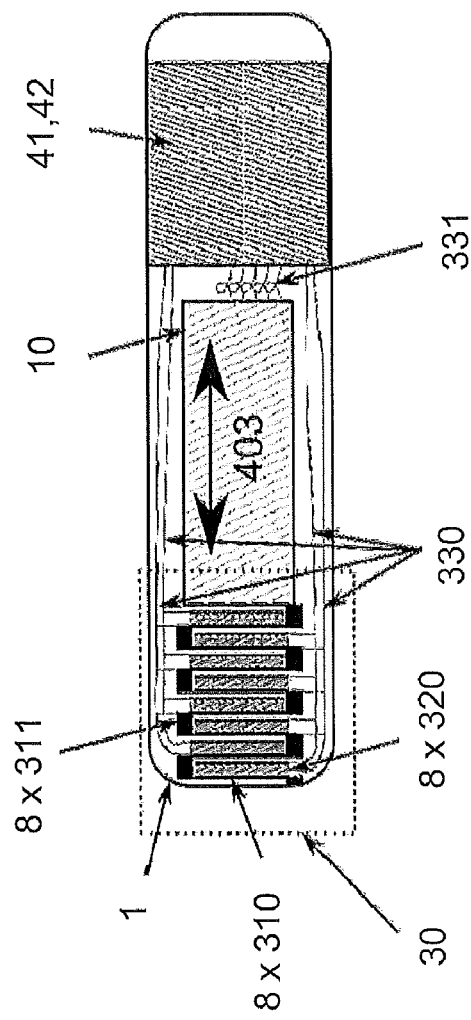
FIG. 5 shows a detailed diagram of a third version of the first embodiment.

The combination of multiple plate springs in the form of a stack, as shown in FIG. 5, is also possible. In this example, eight springs 310 are each combined with one piezoelectric converter 320 and allow translation 403 of the mass 10. Four piezo elements are connected in parallel electrically. A series circuit is also possible. The rigid connections 311 of the springs undergo only minimal deformation with the movement 403 and thus the main deformation takes place in the springs 310 and therefore also in the piezoelectric elements 320.

Figure 6:
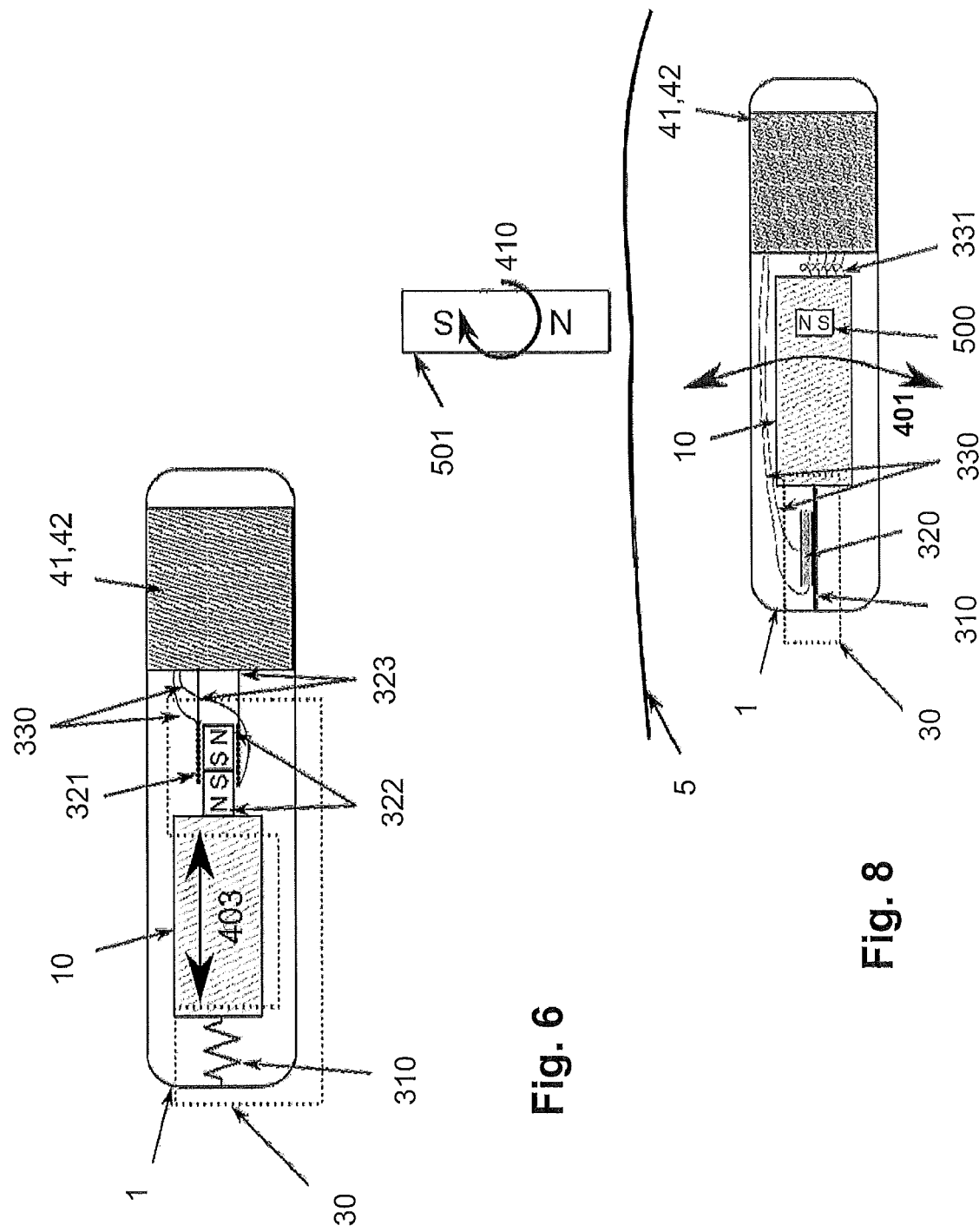
FIG. 6 shows a detailed diagram of a fourth version of the first embodiment.

An implant having a mechanical-electric converter may also have the design described below and illustrated in FIG. 6. The mass 10 is connected to the implant housing 1 via the coupling system 30. The coupling system consists of two components: the spring element 310 and an electromagnetic converter formed by a coil 321, two magnets 322, a holder 323 and electric lines 330. Due to the movement 403 of the mass 10, the magnets 322 move and a voltage is induced in the coil 321. This voltage is transmitted over the lines 330 to the implant electronic system 41 and may be used there or stored in the power reservoir 42.

This design is also highly variable, and the number and arrangement of magnets and coils may be modified in a variety of ways. For example, the coils may be attached to the mass and the magnets may be fixedly connected to the implant. This prevents eddy current losses due to the movement of the magnets. The spring element 310 and the mechanical-electric converter may also be arranged coaxially, for example.

Figure 7:
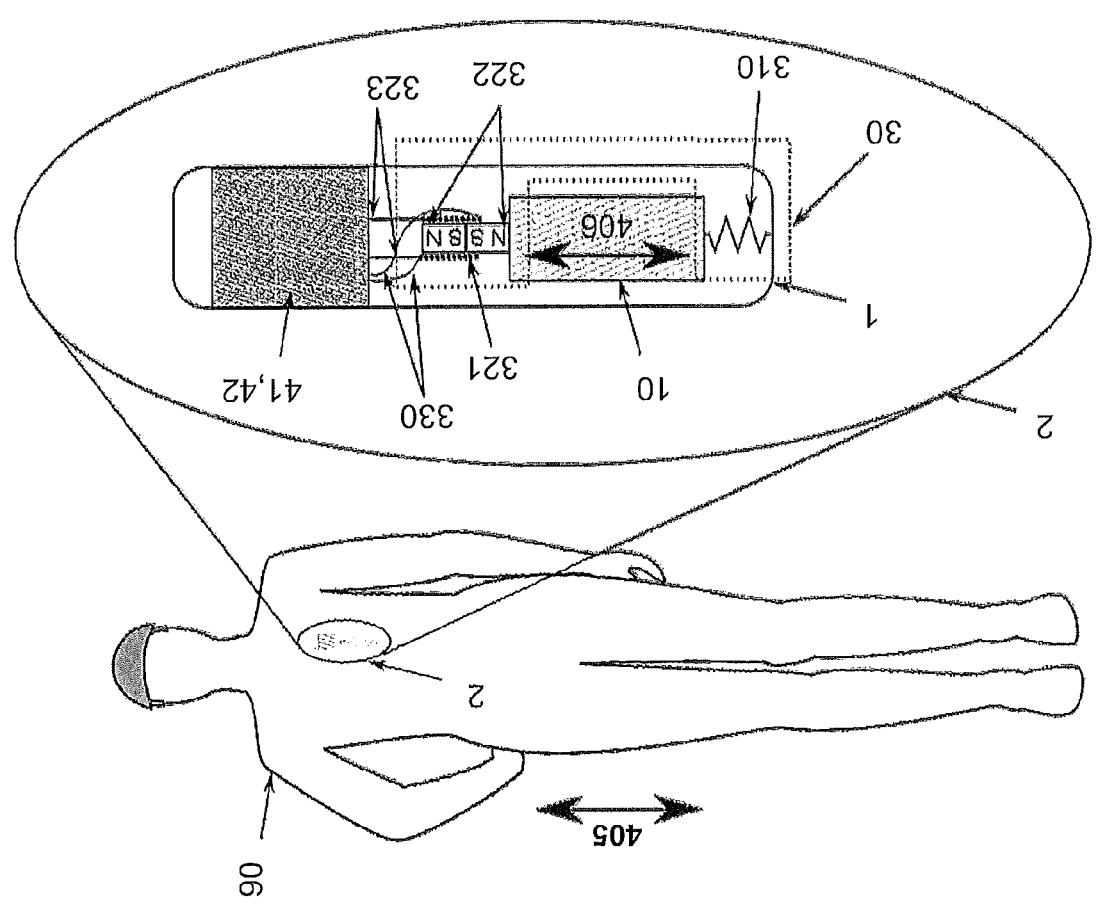
FIG. 7 shows a diagram of the placement and functioning of the last above-mentioned embodiment in a patient's body.

The functioning of an implant having a vibration-capable mass in patients is as follows, as illustrated schematically in FIG. 7. A patient 90 having an active implant 1 in a body area 2 moves up and down 405, e.g., due to running. Since the housing 1 of the implant is in direct contact with the body of the patient 90, it is also moved. The moving mass 10 in the implant then moves 406 relative to the implant housing, so the mechanical-electric converter generates electricity.

If the patient is inactive and has a weak natural movement, then a relative movement 406 of the mass 10 with respect to the implant housing can be induced, e.g., by a movement of the bed created specifically for this purpose, thereby generating electricity in the implant.

The movable mass 10 may also be excited to vibrate by other alternating fields, as diagrammed in FIG. 8. For example, a magnetic field 500 may be part of the moving mass. Through the change in the magnetic field, a force or torque may be transferred to the mass 10, which then moves, and the converter generates electricity. The change in the magnetic field may also be generated by the movement of a strong magnet outside of the patient. The illustration shows a magnet 501, which is outside of the body 5 and is rotated in the manner indicated by the arrow 410.

Figure 9:
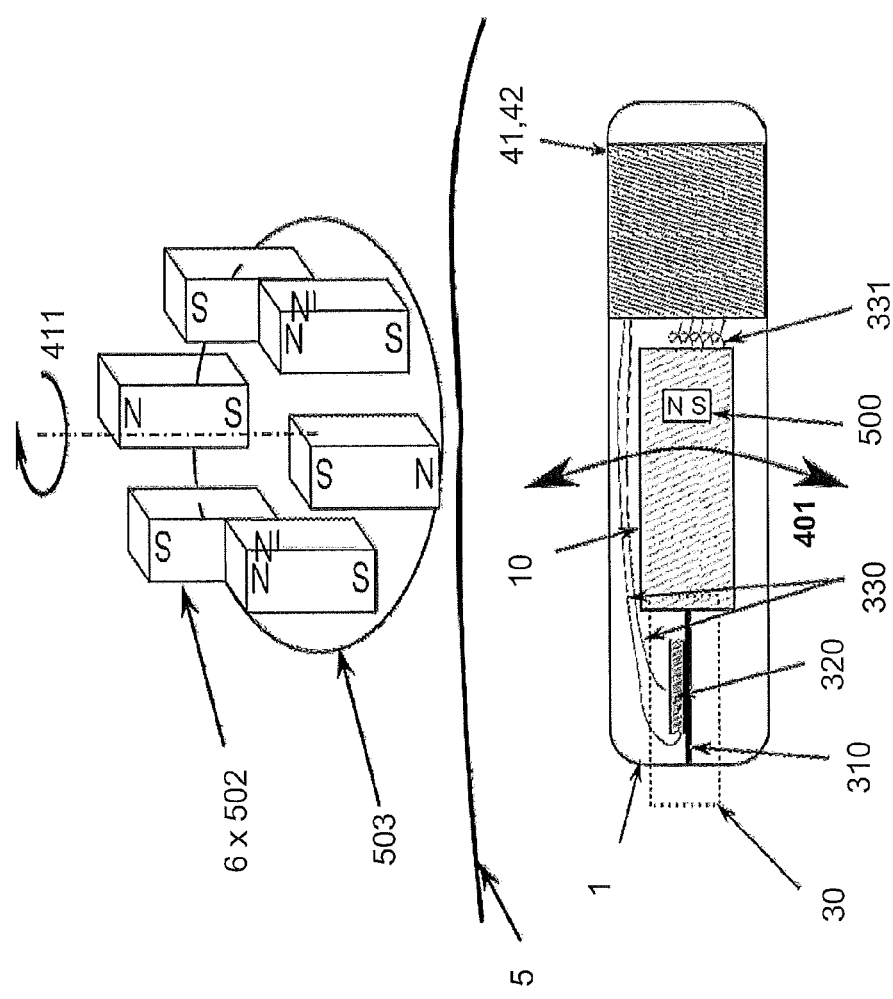
FIG. 9 shows another modified version of this implant.

Alternatively, multiple magnets having alternating alignments may also be moved over the implant, as illustrated in FIG. 9. Outside of the body 5 here, there are six magnets 502, which are mounted on a disk 503. The disk rotates in the direction of the arrow 411. An alternating magnetic field is generated by the rotational movement, and the movable mass 10 can be excited to vibrate.

Figure 10:
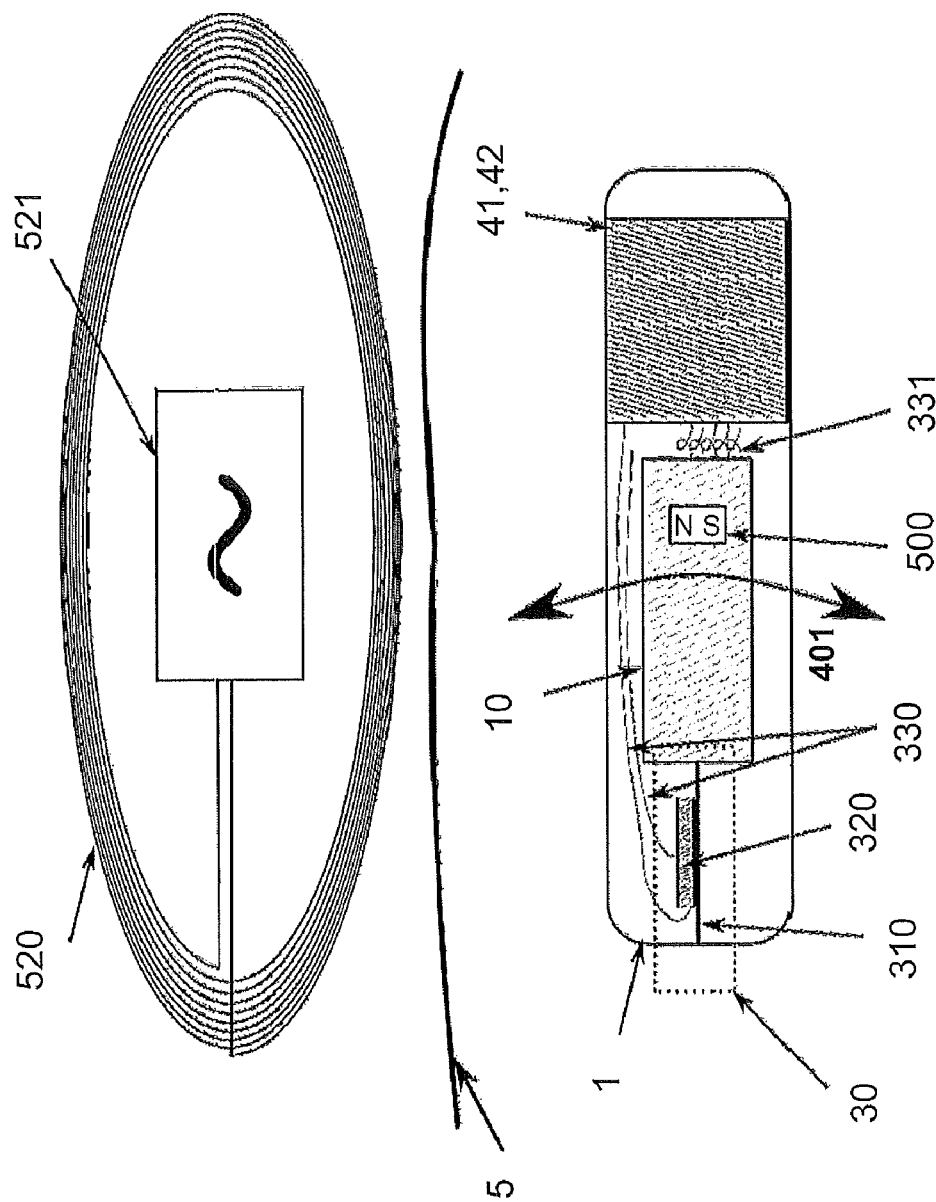
FIG. 10 shows a diagram of another modified version.
Figure 11:
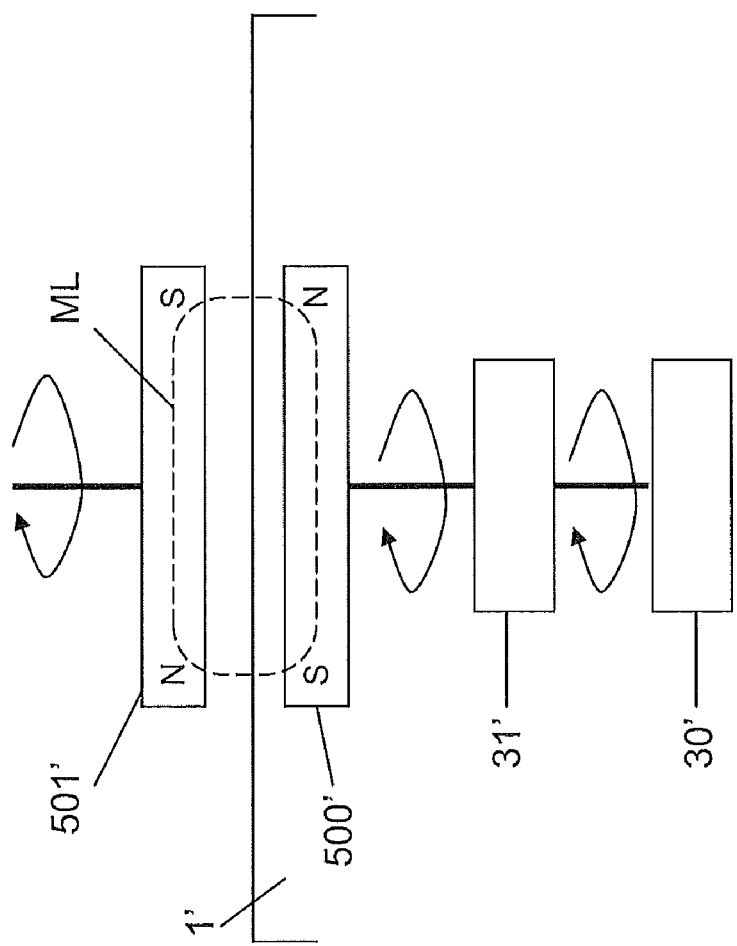
FIGS. 11 to 13 show diagrams of various versions of another embodiment of the invention.

The alternating magnetic field may also be generated by a time-dependent flow of current through a coil, as diagrammed schematically in FIG. 10. A voltage generator 521 generates a signal form. The output of the generator is thus connected to a coil 520 and generates a time-dependent current flow in the coil, which in turn generates a time-dependent magnetic field. The alternating magnetic field interacts with the magnet 500 of the movable mass 10 in the implant 1 and excites the mass to vibrate. The energy of vibration is converted by a coupling system 30 into electricity.

The advantage of generating alternating fields by moving magnets is the low frequency of the system, which leads to less heating of the housing and of the tissue due to eddy currents.

In the case of excitation of the mechanical vibration-capable system from the outside, there is the possibility of closed-loop control of the mechanical vibration in the interior of the implant from outside of the body. Through such a closed loop, the position or frequency of the excitation for example, can be coordinated with the implant to ensure the best possible energy transfer.

The information may be transmitted (unidirectionally or bidirectionally) out of the implant, e.g., inductively or by RF communication. For example, the power consumed by the implant, the voltage or a similar parameter may be transmitted. Transmission of the phase of the energy received is also appropriate because in this way the excitation frequency can be set at the natural frequency of the vibration-capable system without having to determine the amplitude ratio. This also functions in vibration-capable systems of a low quality.

The closed loop may go directly from the implant to the vibration-exciting system, which then optimizes the position or adjusts the excitation frequency. However, the open loop may also pass through the patient. For example, the vibration-exciting system may analyze the data from communication with the implant and transmit information to the patient. This may be accomplished by optical or acoustic signals, for example, which show the patient a better charging position. Various tones are also conceivable as acoustic signals, the variation therein (amplitude, frequency, tone sequence, melody, etc.) indicating the quality of the transmission. Speech information may also be output.

The vibration-capable system in the sense of the present invention may be formed by a rotating spring (e.g., a spiral spring) and a mass. The mass is attached to the spiral spring in such a way that the center of gravity is not on the axis of rotation. The rotational vibration may also be excited by a linear movement. The distance between the axis of rotation and the center of gravity of the mass is as large as possible to obtain a low natural frequency.

In addition to the spiral spring, a piezoelectric converter is also integrated into the vibration-capable system. It deforms as soon as the system vibrates and then generates electricity. The spiral spring itself may also contain one or more piezoelectric converters, which supply electricity.

An electromagnetic system which functions like a dynamo may also be used as the mechanical-electric converter in the implant. The relative movement between a coil system and one or more magnets creates a variable magnetic field in the coil system. The resulting voltage can be used to generate electricity for the implant.

The electromagnetic rotary converter may be embodied so that the coil system is fixedly connected to the implant and the magnetic system is rotatably mounted. The magnetic system may then be excited from the outside to vibrate, inducing a voltage in the coil system.

The principle of magnetic coupling is utilized in another embodiment. An external rotating magnet 501' (outside of the patient) entrains a magnet 500' that is rotatable in the implant 1', as diagrammed in FIG. 1. This also functions if only a magnetic material of a high permeability is used instead of the magnet in the implant 1', so the magnetic field lines ML are well-bundled here and thus the force/torque transmission is optimal. This magnetic material thus implements a magnetic field line bridge (hereinafter referred to as bridge). In a preferred embodiment, such a metal is mu-metal. The arrangement may also be constructed in reverse, namely in such a way that the magnet is in the implant and the magnetic material of a high permeability is outside. However, the preferred embodiment is the one in which no magnet need be used for this purpose in the implant.

To allow a high torque to be transmitted, the radius of the arrangement rotating in the implant is preferably selected to be as large as possible (i.e., as large as the inside dimensions of the implant allow at the maximum).

To prevent eddy currents, the rotational speed of the magnets must be very low. However, a high rotational speed is advantageous if this rotational movement inside the implant is to be converted into electric voltage via an electromagnetic converter (e.g., dynamo) 30', because according to the law of induction, the induced voltage increases with the angular velocity. A step-up gear 31' may be used for this purpose.

Figure 12:
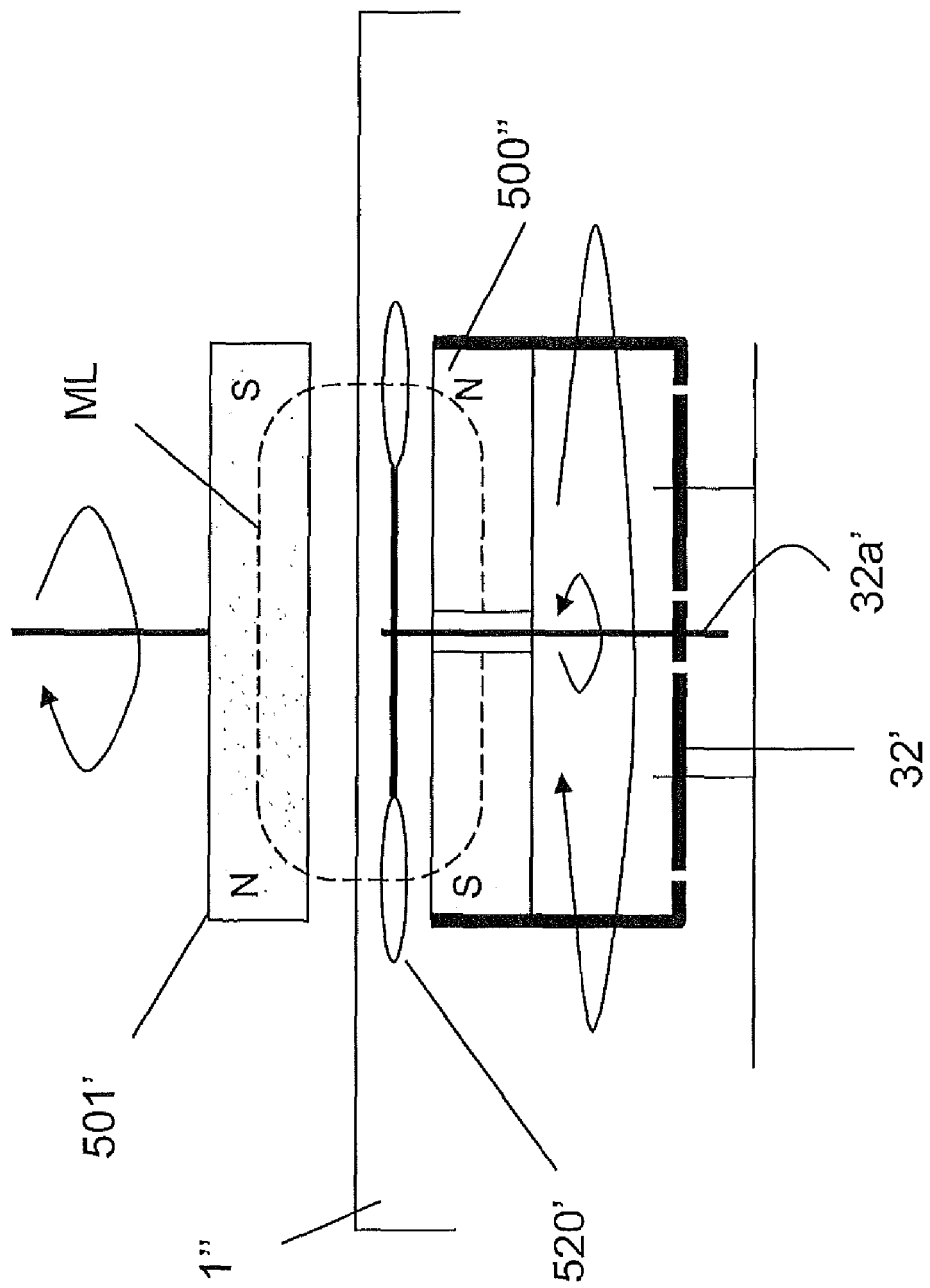

In another embodiment as diagrammed in FIG. 12, the magnetic field implementing the transfer of torque may itself be utilized to induce voltages in coils 520'. These coils must then move in the implant 1" in relation to the magnetic field. Specifically a planetary gear 32' is used for this purpose, serving firstly as a step-up gear, and secondly converting the rotational movement opposite the rotational movement of the rear magnets 500". The angular speeds are thus additive, i.e., the relative movement is more pronounced, which results in a higher induced voltage.

The voltage of the rotating coils 520' is picked up by loop contacts (not shown). The axis may preferably be implemented in such a way that it consists of two halves not electrically connected, so that the voltage can be picked up easily via the bearing of the gear. The bearings are preferably made of brass. This offers good antifriction properties as well as electric contact. Electric contacts via one or more ball bearings made of conductive materials or via conductive liquids that bridge a gap are also conceivable.

Figure 13:
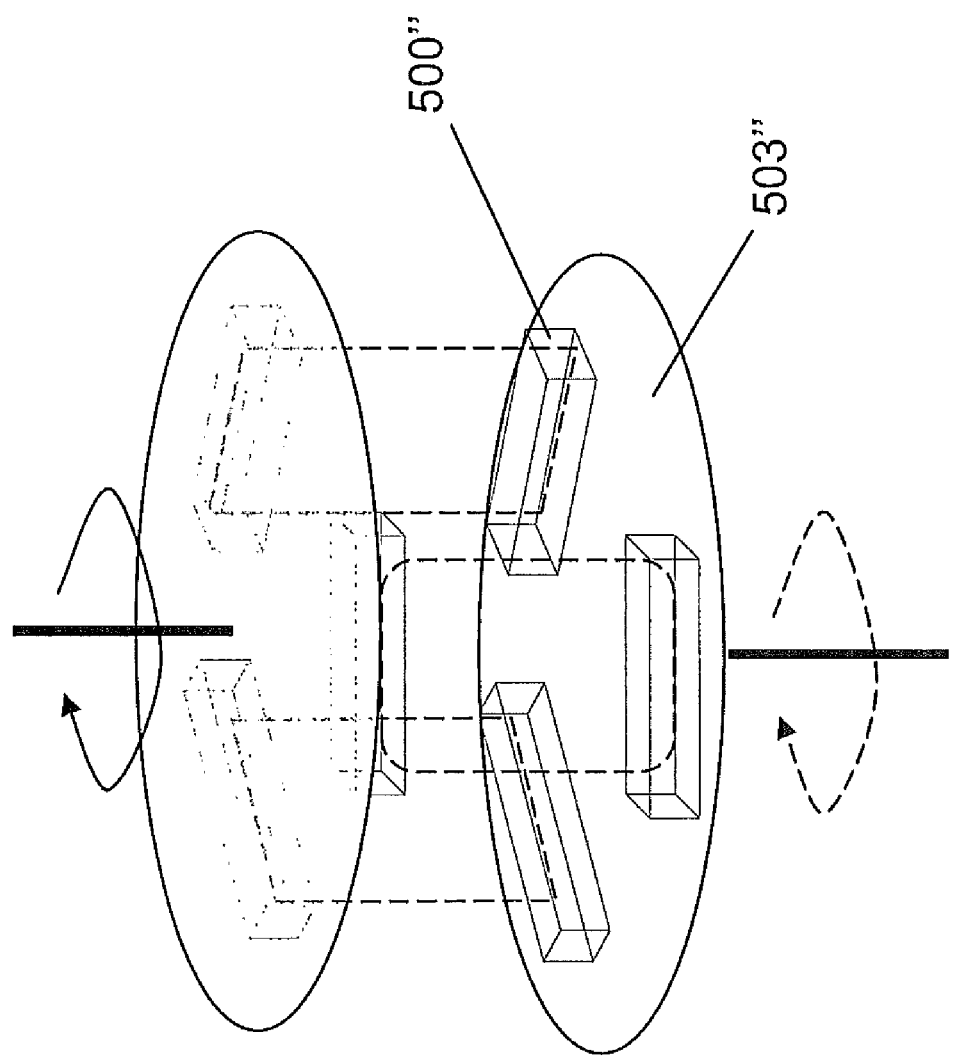

In another advantageous arrangement, multiple magnetic pairs 500" or magnet bridge pairs are each arranged on a disk 503" as illustrated in FIG. 13. This increases the size of the transmissible torque.

In another embodiment, an open-loop mechanism, which regulates slippage, is also provided. To do so, the voltage characteristic induced in the coils is communicated from the implant to the outside by telemetry. The slippage may thus be calculated from amplitudes and phase ratios, and the rotational speed of the extracorporeal rotation can be re-regulated.

To minimize the overall height of the coils, planar coils or coil arrangements are preferred. For example, they may be coiled or also manufactured as monolithic components.

Instead of rotating coils, stationary coils may also be used (in an embodiment that is not shown here). The magnetic flux through the coil surface is varied over time due to the movement of the magnets. For rapid changes in magnetic flux, the principle of the step-up gear described above may also be used. A magnetic bridge rotates rapidly. The magnetically coupled magnets in the implant rotate only at the angular velocity of the external magnets and do not generate any eddy currents. Whenever the bridge closes a magnetic circuit, there is a very great change in the magnetic flux in the coil, which is in the gap at that moment, and a high voltage is induced. In addition to electric contacting of the coils, the positioning of the coils is an advantage of this embodiment. These may be introduced into the magnetic field in a very thin gap, where the magnetic flux, the gradient and the resulting induced voltage are higher than in a wide gap.

This embodiment of the invention is not limited to the examples described above and the aspects of the invention that have been emphasized, but instead permits a variety of modifications within the scope of technical expertise.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

We claim:

1. An active medical implant comprising:
a medical electronic device having a power supply, the medical electronic device including a mechanical vibrator and/or rotor that is induced to vibrate and/or rotate by external excitation from a source external to a patient having the active medical implant implanted therein to generate kinetic energy, wherein the vibrator and/or rotor is energetically connected to an electronic consumption mechanism and/or an energy storage mechanism, such that a portion of the kinetic energy generated with the vibration and/or rotation of the vibrator and/or rotor is input into the electronic consumption mechanism and/or the energy storage mechanism,
wherein the vibrator is designed to be vibration-capable in more than one direction.

2. The active medical implant according to claim 1, further comprising a mechanical-electric converter connected to the vibrator and/or rotor, wherein the energy storage mechanism includes a reservoir of electricity.

3. The active medical implant according to claim 2, wherein the reservoir of electricity includes a battery or capacitor.

4. The active medical implant according to claim 2, wherein the mechanical-electric converter includes a piezoelectric element.

5. The active medical implant according to claim 2, wherein the mechanical-electric converter includes an electromagnetic converter, and wherein the implant further comprises a torque converter optionally connected upstream from the electromagnet converter.

6. The active medical implant according to claim 5, wherein the electromagnetic converter comprises a coil-magnet arrangement or a generator.

7. The active medical implant according to claim 1, wherein the energy storage mechanism includes a mechanical energy storage mechanism, and wherein a mechanical-electric converter for converting stored mechanical energy into electric operating power for the patient is connected to the mechanical energy storage mechanism.

8. The active medical implant according to claim 7, wherein the mechanical energy storage mechanism comprises a flywheel.

9. The active medical implant according to claim 1, wherein the vibrator and/or rotor is arranged in a shared housing with the operative electric components of the implant.

10. The active medical implant according to claim 1, wherein the vibrator and/or rotor is arranged outside of a housing containing the operative electric components of the implant and in a portion of a body with a high intensity of movement of the patient wearing the implant, the vibrator and/or rotor electrically connected to the housing of the operative electric components.

11. The active medical implant according to claim 1, wherein the vibrator and/or rotor comprises multiple vibrators and/or rotors having different directions of vibration and/or axes of movement and/or different natural frequencies.

12. The active medical implant according to claim 1, wherein the more than one direction comprises three dimensions.

13. The active medical implant according to claim 1, wherein the vibrator has an independently variable direction of vibration and/or the rotor has an independently variable axis of rotation.

14. The active medical implant according to claim 13, wherein the vibrator with the variable direction of vibration and/or the rotor with the variable axis of rotation includes means for adjusting the direction of vibration and/or the axis of rotation as a function of the body position and/or movements of the patient wearing the implant.

15. The active medical implant according to claim 1, wherein the vibrator and/or rotor comprises function components and/or carrying components of the implant, which are suspended in a housing so they are vibration-capable and/or vibratable.

16. The active medical implant according to claim 15, wherein the vibrator and/or rotor comprises a carrying frame of the implant having the function components mounted therein.

17. The active medical implant according to claim 1, wherein the vibrator and/or rotor is designed to receive the external excitation at a frequency tuned to its natural frequency.

18. The active medical implant according to claim 17, wherein an electric mechanical converter for excitation by an external alternating electromagnetic field is connected to the externally excitable vibrator and/or rotor.

19. The active medical implant according to claim 18, wherein the electric mechanical converter comprises a piezo element or an electromagnetic converter.

* * * * *